United States Patent
Sabahi et al.

(10) Patent No.: US 6,489,524 B1
(45) Date of Patent: Dec. 3, 2002

(54) SELECTIVE BROMINATION OF AROMATIC COMPOUNDS

(75) Inventors: Mahmood Sabahi, Baton Rouge, LA (US); Hassan Y. Elnagar, Baton Rouge, LA (US); Robert L. Davis, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 580 days.

(21) Appl. No.: 08/957,901

(22) Filed: Oct. 27, 1997

(51) Int. Cl.[7] .................. C07C 17/04; C07C 21/14; C07C 17/20; C07C 17/16

(52) U.S. Cl. ................ 570/181; 570/182; 570/260; 570/261

(58) Field of Search ................ 570/260, 261, 570/181, 182

(56) References Cited

PUBLICATIONS de la Vega, F., et al, "Highly selective bromination of toluene in a bromine–oxirane–zeolite system", *Zeolites*, 1993, vol. 13, pp. 341–347.

de la Vega, F., et al, "Selective para–Bromination of Toluene catalysed by Na–Y Zeolite in the Presence of an Epoxide", *J. Chem. Soc. Chem. Commun.*, 1989, pp. 653–654.

Smith, K., et al., "Highly efficient para–selective bromination of simple aromatic substrates by means of bromine and a reusable zeolite", *Chem. Commun.*, 1996, pp. 467–468.

*Primary Examiner*—Cecilia Tsang
*Assistant Examiner*—Ebenezer Sackey
(74) *Attorney, Agent, or Firm*—Edgar E. Spielman, Jr.

(57) ABSTRACT

Aromatic substrates are Ar-brominated in high yield and selectivity by reacting the substrate with a brominating agent in the presence of at least about 0.19 gram per mmol of substrate of a zeolite catalyst which has an absorbed water content of no greater than about 7.5 weight percent.

20 Claims, No Drawings

SELECTIVE BROMINATION OF AROMATIC COMPOUNDS

TECHNICAL FIELD

This invention relates generally to the selective aromatic bromination (Ar-bromination) of aromatic substrates, and more specifically to an improved process for the selective para-bromination of benzene derivatives in the presence of a shape selective zeolite catalyst.

The selective para-bromination of toluene, catalyzed by NaY zeolite in the presence of an epoxide, has been reported by F. de la Vega et al., *J Chem. Soc., Chem. Commun.*, 1989, 653. The ratio of p- and o-isomers obtained was 98 to 2, but only about 10 to 13 percent of the toluene was converted. In experiments using no epoxide or in the presence of carbonates, the reaction proceeded to completion but the final para-selectivity was only 67%. The amount of zeolite catalyst used was about 0.09 gram per mmol of toluene. It was stated that adding a fresh batch of catalyst made the reaction resume with the same selectivity, but the final conversions obtained are not reported.

The para-selective bromination of benzene derivatives, such as toluene, using shape-selective zeolite catalysts, for example, NaY, HY, and NaX zeolites, has also been described by K. Smith et al., "Highly efficient para-selective bromination of simple aromatic substrates by means of bromine and a reusable zeolite", *Chem. Commun.*, 1996, 467–468. In contrast to de la Vega, much larger amounts of zeolite were used in order to obtain complete conversion. When NaY zeolite was used in an amount of 0.55 gram per 0.85 mmol of toluene (0.65 gram per mmol), it was reported that 98% absolute yields of p-bromotoluene were obtained. The yield of para-brominated products which can be achieved is also indicated to depend upon the type of zeolite used. For example, NaY zeolite gave better conversion (yield) than using the same amount of a NaX zeolite in producing p-bromotoluene. Smith et al. claim that the zeolite catalysts can be regenerated by calcination, but it is not believed that calcination returns the zeolites to their original state. In any event, the relatively large amount of catalyst required to be regenerated would make this process too expensive to be practical from a commercial standpoint.

It has now been found that the absorbed water content of the zeolite has a significant effect on the yield and selectivity when producing p-brominated benzene derivatives. In fact, water saturated zeolites favor chain bromination over ring substitution. We have found that maintaining the absorbed water content of the zeolite below a certain level, which varies depending upon the particular zeolite used, permits high selectivity and yields to be achieved using much smaller amounts (about one-half as much) of zeolite than required by Smith et al.

SUMMARY OF INVENTION

In accordance with this invention, there is provided a process for selectively Ar-brominating an aromatic substrate comprising reacting said substrate with a brominating agent in the presence of at least about 0.19 gram per mmol of said substrate of a zeolite catalyst which has an absorbed water content of no greater than about 7.5 weight percent.

The zeolite catalysts for use in the process of the invention are chosen such that the aromatic substrate will fit into the pores of the zeolite. This permits bromination to occur within the pores where access to sites on the substrate other than the desired position is hindered. Accordingly, such zeolite catalysts are termed as being "shape selective". For simple aromatic compounds such as, toluene, fluorobenzene, and isobutylbenzene, faujasites (e.g., NaX, HY, and NaY zeolites) which have a pore (aperture) size of about 7 angstroms give para-brominations in high yield and selectivity provided the zeolites are dried and kept dry. The optimum pore size for the selective bromination of other aromatic substrates is selected depending upon the size and shape of the molecules to be brominated. In general, the pore size should range from about 6 to 8 angstroms and preferably from about 6.5 to 7.5 angstroms. The most preferred types of zeolite for use in the process of the invention are NaX and NaY zeolites. Such zeolites are well known—for example, type X zeolites corresponding to the typical formula:

and type Y zeolites corresponding to the typical formula:

where a portion of the sodium cation could be substituted by other cations such as $K^+$, $Ca^{++}$, $Mg^{++}$, $Ba^{++}$, $Zn^{++}$, and $Fe^{++}$. Proton form zeolite catalysts, such as HY zeolites, as well as mixtures of cation and proton form zeolites, can also be used.

The pores of the zeolite particles, where the selective bromination process takes place, should be kept substantially free of absorbed water. Accordingly, in practicing the process of the invention, the zeolites should have an absorbed water content of no greater than about 7.5 weight percent, preferably no greater than about 5.0 weight percent, and most preferably less than 5 weight percent water, based on the total weight of zeolite and water. As used in the specification and claims herein, by "absorbed water content" is meant the weight percent of water which can be removed by drying the zeolite at a temperature of from 240–250° C. at a pressure of from 0.1–0.05 mm Hg for 4 hours. The zeolite may also contain additional water which requires higher temperatures for removal. Although it is not possible to distinguish between water of hydration and absorbed water, for the purpose of this invention the residual water content of the zeolites which is not removed by the 240–250° C. drying procedure is considered to be water of hydration. The complete removal of this residual water might further improve the shape selectivity function of the zeolite. However, the presence of the residual water does not prevent the achievement of good yields and selectivity when using much smaller amounts of catalyst than are required by the prior art process. It is important that the dried zeolites be protected against excessive exposure to atmospheric moisture prior to use, because the zeolites may pick up sufficient moisture during handling, or even when kept in a desiccator for a few days, so as to significantly decrease their effectiveness. NaX zeolites appear to be more sensitive to absorbed water content than NaY zeolites.

The zeolites used in the examples below contained varying amounts of absorbed water when received from the vendor. Absorbed water was removed by drying the zeolites at a temperature of 240–250° C. for four hours at a reduced pressure of from about 0.1 to 0.05 mm Hg. Thermogravimetric analysis (TGA) under nitrogen from 20–900° C. removes not only the absorbed water, but also the water of hydration. Although such high temperature drying conditions could be used, it was found that the drying procedure at 240–250° C. and reduced pressure is sufficient to achieve good yields and selectivity.

In order to illustrate the ready water absorption by zeolites, vendor samples of NaY and NaX zeolites were tested for water content by TGA from 20–900° C. under nitrogen. A sample of NaY zeolite as received from the vendor contained 24–25 wt % water. After drying at 240–250° C. and 0.1–0.05 mm Hg for four hours, analysis by TGA under nitrogen showed a rapid water pick up of about 6.4 wt % at temperatures below 100° C. When again heated to 900° C., the sample lost this water followed by an additional 5.2 wt %, indicating that the "dry" zeolite still contained about 5.2 wt % water.

A sample of NaX zeolite as received from the vendor contained 7.3 wt % water. After drying at 240–250° C. as described above, the sample showed a fast water absorption of 3.1 wt % during handling. When again heated to 900° C., it lost this absorbed water followed by an additional loss of 7.3 wt % indicating that the "dry" zeolite contained 7.3 wt % water.

In order to examine the rate of water absorption by "dry" zeolite, we exposed one gram samples of dried NaY zeolite in dry 20 mL vials to laboratory air and the water gain was measured gravimetrically. Even after 24 hours at these conditions, the zeolite picked up a maximum of 0.4 wt % water. The small exposed surface area and the generation of a protective layer of wet zeolite on top could be the reason for the slow rate of water absorption. When this experiment was carried out with the zeolite in a dish, such that the zeolite had a larger exposed surface area, with occasional mixing, the zeolite was saturated (25 wt %) with absorbed water in 5 hours. When the zeolites were exposed to the atmosphere in a container having a large surface area, they became saturated with 25 wt % of absorbed water over a relatively shorter period of time. These experiments demonstrate the need to store and handle the zeolites in a manner which avoids excess water pick-up prior to use.

The amount of zeolite catalyst used is preferably selected to give the best yield and selectivity for any particular catalyst and aromatic substrate combination. A minimum amount of at least about 0.19 gram of zeolite per mmol of substrate, and preferably a minimum amount of at least about 0.3 gram of zeolite per mmol of substrate should be used in order to obtain substantially complete conversions with good selectivity. For economic reasons, the amount of zeolite should be kept to the minimum consistent with good yields and selectivity. In any event, good yields and selectivity can be obtained using less than the 0.65 gram per mmol of substrate required by the prior art.

The aromatic substrates which can be selectively brominated by the process of the invention include polycyclic aromatic compounds such as naphthalene as well as benzene compounds. The invention is particularly useful in the para-bromination of benzene derivatives. Non-limiting examples of such derivatives include $C_1$ to $C_{10}$ (preferably $C_1$ to $C_4$) alkyl substituted arenes or halogenated benzene compounds such as toluene, fluorobenzene, isobutylbenzene, tert-butylbenzene, ethylbenzene, cumene, chlorobenzene, bromobenzene and the like.

Any agent that is capable of producing electrophilic bromonium ion ($Br^+$) can be used in the bromination process. Examples of such agents include bromine ($Br_2$), N-bromosuccinimide (NBS), dibromodimethyl hydantoin and BrCl. It is preferred that when bromine is used in the process of this invention, it should be essentially anhydrous, i.e., contain less than 100 ppm by weight water, and contain no more than 10 ppm by weight of organic impurities, e.g., oil, grease. carbonyl-containing hydrocarbons, iron, and the like. With such a bromine purity, there is little, if any, impact on the color attributes of the products. Available, commercial grade bromine may have such purity. If, however, such is not available, the organic impurities and water content of the bromine can be conveniently reduced by mixing together a 3 to 1 volume ratio of bromine and concentrated (94–98 percent) sulfuric acid. A two-phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

The bromination process is carried out in an organic solvent medium. The organic solvent medium used for the bromination process should be anhydrous and inert to the reactants. Preferred solvents include acetonitrile and halogenated, saturated aliphatic hydrocarbons such as lower alkyl halides—for example, carbon tetrachloride, chloroform, tetrachlorethane, bromochloromethane, methylene chloride, trichloroethane, dibromoethane, dibromomethane, ethylene dichloride, and the like.

Amounts of solvent are used so as to provide a concentration of from about 10 to 100 grams of solvent per gram of aromatic substrate. The amount of brominating agent used is preferably in slight excess (e.g., about 5 to 10%) to the stoichiometric amount needed to substitute a single bromine atom onto the aromatic ring. The order of addition of reactants can be varied, but at least in some cases, it was found that adding bromine to zeolite prior to adding the aromatic reactant resulted in lower conversions when compared to adding the bromine to a mixture of zeolite and reactant.

Preferred reaction temperatures range from about 0 to 70° C. The reactions are usually complete in from about 1 to 4 hours. After the bromination reaction is complete, the product can be recovered and purified, if necessary, using conventional techniques. For example, the zeolite is separated by filtration and the filtrate is washed with a 20% by weight solution of aqueous sodium sulfite and then dried either by azeotropic distillation or by the use of a drying agent such as magnesium sulfate. The zeolite can be regenerated for reuse by treatment first with dilute sodium hydroxide solution and then with water and heating in nitrogen at 400 to 450° C. for from 1 to 3 hours or at 240–250° C. and 0.1–0.05 mm Hg for 2–3 hours.

The invention is further illustrated by, but is not intended to be limited to, the following examples.

EXAMPLE 1

Bromination of Toluene in the Presence of NaY and NaX Zeolites with Varying Amounts of Water Zeolite samples containing 5, 10, 15, and 25 wt % absorbed water were prepared. Toluene (1.6 mmol, 147 mg) and NaY zeolite having a pore size of about 7 angstroms (1.0 g, 0.63 g per mmol of toluene) were added to dry ethylene dichloride (EDC, 10 mL) in 20 mL vials and stirred at 40° C. for 15 minutes. Bromine (1.9 mmol, 304 mg in 2 mL EDC) was added and the mixture stirred at 40° C. for 2 hours. Samples were removed and analyzed by gas chromatography. The same procedure was used to brominate toluene using a NaX zeolite having a pore size of about 7 angstroms, except that dry dichlioromethane was used as the solvent and the reaction was carried out at room temperature. Although lights were off in the hood during the reactions, no extra precautions were taken to protect the reactions from light unless specified. Also, in the case of wet (25 wt % water) zeolite, in several experiments, oxygen was bubbled into the reaction mixture before the addition of bromine in an attempt to retard the free radical reactions. The results (GC% area) are summarized in Tables 1 and 2.

TABLE 1

Bromination of toluene with bromine and NaY zeolite

| Water, wt % | % Toluene | % OBT* | % PBT** | % BB*** | % Dibromo**** |
|---|---|---|---|---|---|
| 25, & O$_2$ | 59 | <1 | 1 | 39 | <1 |
| 25 | 90 | <1 | 1 | 8 | trace |
| 15 | 61 | 4 | 23 | 12 | trace |
| 10 | trace | 3 | 97 | trace | trace |
| 5 | trace | 2 | 98 | trace | trace |
| <5 | trace | 1 | 99 | trace | trace |

*o-bromotoluene
**p-bromotoluene
***benzylbromide
****dibromo compounds

TABLE 2

Bromination of toluene with bromine and NaX zeolite

| Water, wt % | % Toluene | % OBT* | % PBT** | % BB*** | % Dibromo**** |
|---|---|---|---|---|---|
| 25 (O$_2$, no light) | 37 | <1 | <1 | 58 | 3 |
| 25 (O$_2$, no light) | 16 | <1 | <1 | 77 | 5 |
| 25, (O$_2$) | 9 | trace | trace | 85 | 5 |
| 25 | 40 | trace | trace | 57 | 2 |
| 15 | 39 | trace | trace | 58 | 2 |
| 10 | 25 | 2 | 16 | 55 | 2 |
| 5 | none | 1 | 98 | none | 1 |
| <5 | none | <1 | >98 | none | trace |

*o-bromotoluene
**p-bromotoluene
***benzylbromide
****dibromo compounds

As shown by the results reported in Tables 1 and 2, selectivity drops with increasing water content. This is more pronounced with NaX zeolite. Competing free radical chain bromination rapidly becomes the main reaction with NaX containing at least 10 wt % water. However, this is not observed with NaY even when saturated with water. Bromination, free radical or ionic, is faster with NaX. This is contrary to the expected rate based on the higher acidity of the NaY zeolite. The para-selectivity is greater for NaX which may result from its higher sodium content. Elimination of light slows down the free radical reaction but does not stop it. These results suggest that NaX zeolite is a better catalyst for the free radical reaction on the side chain.

EXAMPLE 2

Effect of Zeolite Loading on Selectivity

Three 20 mL vials were charged with 0.1, 0.3, and 0.6 g of dried (<5 wt % absorbed water) HY zeolite. Another three vials were charged with the same amounts of dried NaY zeolite. Dry dichloromethane (10 g) and toluene (1.6 mmol, 147 mg) were added to each vial generating mixtures which contained 0.06, 0.19, and 0.38 g of zeolite per mmol of toluene, respectively. Bromine solution (1.9 mmol, 304 mg in 2 mL of dry dichloromethane) was added to each vial and stirred at room temperature. The reactions were sampled after 3 and 5 hours and analyzed by GC. For 0.1, 0.3, and 0.6 g of HY zeolite the p/o ratios were 84/12, 88/12 and 88/12, respectively. However, for 0.1, 0.3, and 0.6 g of NaY zeolite, the p/o ratios were 84/16, 91/9 and 97/3, respectively.

Complete conversions were observed in reactions using 0.3 g and 0.6 g of zeolites and only 82% conversion was obtained using 0.1 g of zeolites. These results demonstrate that when using dry NaY zeolite, a p/o selectivity of 91/9 and high conversion (about 100%) can be achieved using as little as about 0.19 gram of zeolite per mmol of toluene. Also, a high selectivity 97/3 and complete conversion were obtained using only 0.38 g of NaY zeolite per mmol of toluene. In contrast, Smith et al., (*Chem Commun*, 1996, 467–468) required about 0.65 g of NaY zeolite per mmol of toluene to obtain a comparable result. Improved selectivity and conversions compared to Smith were also achieved using smaller amounts of the dried HY zeolite.

EXAMPLE 3

Selectivity vs. Reaction Progress with NaX

The selectivity of the bromination of isobutylbenzene (IBB) in the presence of NaX zeolite was assessed relative to the progress of reaction. Specifically, to a mixture of IBB (0.064 mol, 8.6 g), dry NaX zeolite (20 g, <5 wt % absorbed water), and methylene chloride (212 g), was added bromine (0.069 mol, 18.4 g of a 60 wt % solution in dichloromethane) in four portions over two hours and the reaction mixture was analyzed by GC. The selectivity was highest after the first bromine addition (p/o=99.6/0.4) and dropped at the end (p/o=99.2/0.8). Analysis of the reaction mixture after stirring at room temperature overnight showed 0.3 wt % IBB, 0.8 wt % ortho, and 98.8 wt % para-bromoisobutylbenzene with a p/o ratio of 99.2/0.8.

For toluene under identical conditions, the observed selectivity at 25% conversion was 98.8/1.2 p/o which dropped to 96.9/3.1 at the end of reaction. Analysis of the reaction mixture at the end of reaction showed 5.5 wt % toluene, 2.9 wt % ortho and 91.5 wt % para-bromotoluene. From the above results, for IBB the selectivity drops slightly, but for toluene it drops faster.

What is claimed is:

1. A process for selectively Ar-brominating an aromatic substrate, said process comprising reacting said substrate with a brominating agent in the presence of at least about 0.19 gram per mmol of said substrate of a zeolite catalyst which has an absorbed water content of no greater than about 7.5 weight percent.

2. The process of claim 1 wherein said zeolite catalyst is selected from the group consisting of NaY, NaX, and HY zeolites which have a pore size of from about 6.5 to 7.5 angstroms, said aromatic substrate is a mono-substituted benzene compound, and the product is a p-brominated benzene compound.

3. The process of claim 2 wherein said monosubstituted benzene is a $C_1$ to $C_{10}$ alkyl-benzene or a halobenzene.

4. The process of claim 3 wherein said monosubstituted benzene compound is toluene, said brominating agent is $Br_2$, said zeolite catalyst has a pore size of about 7 angstroms, and the product is p-bromotoluene.

5. The process of claim 1 wherein said substrate is reacted in the presence of at least about 0.3 gram of zeolite per mmol of substrate.

6. The process of claim 1 wherein said absorbed water content is less than 5 weight percent.

7. The process of claim 5 wherein said zeolite is a NaX or NaY zeolite having a pore size of about 7 angstroms, said aromatic substrate is a monosubstituted benzene compound and the product is a p-brominated benzene compound.

8. The process of claim 7 wherein said aromatic substrate is toluene which is converted to p-bromobenzene in a yield of at least about 97%.

9. The process of claim 7 wherein said monosubstituted benzene compound is selected form the group consisting of toluene, ethylbenzene, cumene, tert-butyl benzene, isobutylbenzene, bromobenzene, chlorobenzene, and fluorobenzene.

10. The process of claim 9 wherein said monosubstituted benzene compound is fluoro-benzene.

11. The process of claim 9 wherein said monosubstituted benzene compound is isobutyl-benzene.

12. The process of claim 1 wherein said zeolite catalyst has a pore size of from about 6 to 8 angstroms.

13. The process of claim 1 wherein said zeolite catalyst is a faujasite.

14. The process of claim 7 wherein said monosubstituted benzene compound is a halogenated benzene.

15. A process for selectively Ar-brominating an aromatic substrate, said process comprising reacting said substrate with a brominating agent in the presence of at least about 0.19 gram per mmol of said substrate of a zeolite catalyst which has been heated in order to obtain a zeolite catalyst which has an absorbed water content of no greater than about 7.5 weight percent.

16. The process according to claim 15 wherein said zeolite catalyst has been heated at a temperature of from about 240–250° C. at reduced pressure.

17. The process according to claim 15 wherein said zeolite catalyst has an absorbed water content of less than 5 weight percent.

18. The process according to claim 16 wherein said zeolite catalyst has an absorbed water content of less than 5 weight percent.

19. The process according to claim 16 wherein said pressure is from about 0.1–0.05 mm Hg and the heating is for 4 hours.

20. The process according to claim 18 wherein said pressure is from about 0.1–0.05 mm Hg and the heating is for 4 hours.

* * * * *